United States Patent [19]

Kugo et al.

[11] Patent Number: 5,304,140
[45] Date of Patent: Apr. 19, 1994

[54] CATHETER FOR INTRODUCTION INTO BLOOD VESSEL

[75] Inventors: Takahiro Kugo; Kazuhito Ishihara, both of Fujinomiya, Japan

[73] Assignee: Terumo Kabushiki Kaisha, Tokyo, Japan

[21] Appl. No.: 465,164

[22] PCT Filed: Aug. 26, 1988

[86] PCT No.: PCT/JP88/00851
§ 371 Date: Feb. 26, 1990
§ 102(e) Date: Feb. 26, 1990

[87] PCT Pub. No.: WO89/01799
PCT Pub. Date: Mar. 9, 1989

[30] Foreign Application Priority Data

Aug. 28, 1987 [JP] Japan ................ 62-214338

[51] Int. Cl.$^5$ .................. A61M 25/00; A61M 5/178
[52] U.S. Cl. ...................... 604/281; 604/164; 604/280; 128/772
[58] Field of Search ............... 604/150, 164, 165, 172, 604/280, 281; 128/772

[56] References Cited

U.S. PATENT DOCUMENTS

| | | | |
|---|---|---|---|
| 3,827,434 | 8/1974 | Thompson et al. | 604/160 |
| 4,033,331 | 7/1977 | Guss et al. | |
| 4,345,602 | 8/1982 | Yoshimura et al. | 128/349 R |
| 4,388,076 | 6/1983 | Waters | 604/165 |
| 4,596,564 | 6/1986 | Spetzler et al. | 604/281 |
| 4,659,328 | 4/1987 | Potter et al. | 604/170 |
| 4,834,709 | 5/1989 | Banning et al. | 604/281 |
| 4,834,725 | 5/1989 | Iwatschenko | 604/281 |
| 4,876,126 | 10/1989 | Takemura et al. | 428/35.7 |
| 4,925,445 | 5/1990 | Sakamoto et al. | 604/95 |
| 4,969,875 | 11/1990 | Ichikawa | 604/158 |
| 4,981,477 | 1/1991 | Schon et al. | 604/281 |
| 5,019,040 | 5/1991 | Itaoka et al. | 604/281 |

FOREIGN PATENT DOCUMENTS

| | | |
|---|---|---|
| 930636 | 7/1973 | Canada ................ 604/281 |
| 0141006 | 5/1985 | European Pat. Off. |
| 0213749 | 7/1986 | European Pat. Off. |
| 2401668 | 8/1977 | France |
| 57-36945 | 2/1982 | Japan |
| 60-63065 | 4/1985 | Japan |
| 60-63066 | 4/1985 | Japan |
| 61-268266 | 11/1986 | Japan |

*Primary Examiner*—John G. Weiss
*Attorney, Agent, or Firm*—Frishauf, Holtz, Goodman & Woodward

[57] ABSTRACT

Disclosed is a catheter which is introduced into a blood vessel for the treatment or inspection of a diseased portion in the blood vessel. For facilitating the introducing operation of the catheter, a super-elastic wire is housed in the catheter body in a manner to extend in the longitudinal direction of the catheter body. The super-elastic wire may be fixed within the lumen of the catheter body, may be detachably provided, or may be embedded in a part of the catheter body. The exposed surface of the catheter body or the super-elastic wire may be covered with a layer of a watersoluble high molecular weight material. Also, an X-ray intransmissible material may be applied to the exposed surface of the catheter body or the super-elastic wire.

5 Claims, 2 Drawing Sheets

CATHETER FOR INTRODUCTION INTO BLOOD VESSEL

TECHNICAL FIELD

The present invention relates to a catheter for introduction into a blood vessel for the treatment or inspection of a diseased portion within the blood vessel.

BACKGROUND ART

A catheter for introduction into a blood vessel is used mainly for injection of a medical solution, a contrast media, etc. into the blood vessel for the treatment or inspection of a diseased portion within the blood vessel. The conventional catheter of this type is constructed such that a hub is simply mounted to the proximal end of a flexible tubular body. For introducing the conventional catheter into a blood vessel, a guide wire is inserted in advance into the blood vessel, followed by introducing the catheter into a desired position within the blood vessel along the guide wire.

The requirement of guiding by a guide wire necessitates a troublesome operation for a long time for enabling the distal end of the conventional catheter to reach a desired position. Also, a blood vessel after branching is bent and diminished in inner diameter, leading to an increased resistance to the catheter insertion. Naturally, it is difficult to insert a guide wire into the branched blood vessel, making it more difficult to introduce the catheter to reach the desired position. Further, a series of operations for insertion and withdrawal of the catheter give serious pains to the patient.

An object of the present invention is to provide a catheter for introduction into a blood vessel, which can be easily introduced even into a branched blood vessel such as a celiac artery without using a guide wire. The catheter of the present invention permits markedly alleviating the pain given to the patient. Also, it is possible to simplify the operation for introducing the catheter into a blood vessel.

DISCLOSURE OF THE INVENTION

In the present invention, the above-noted problems inherent in the prior art are solved by disposing a super-elastic wire within a tube or a tubular material forming a catheter body such that the wire extends in the longitudinal direction of the tube.

According to the present invention, there is provided a catheter for introduction into a blood vessel, comprising a catheter body and a super-elastic wire housed in the catheter body in a manner to extend along the catheter body.

Where the super-elastic wire is disposed within a lumen of the catheter body, the wire may be coated with a synthetic resin and, further, with a water-soluble high molecular weight material. The outer surface of the catheter body may also be coated with a water-soluble high molecular weight material so as to reduce the resistance by friction with the inner wall of the blood vessel. It is also possible to mix an X-ray intransmissible material with the resin used for coating the catheter body or super-elastic wire. In this case, the catheter introducing operation can be performed while observing the image of the catheter formed by the X-ray. Further, the super-elastic wire may be detachably mounted to the catheter body.

Further, the super-elastic wire may be embedded in a part of the catheter body, or may be detachably mounted within a lumen of the catheter body. Still further, it is desirable to bend in advance the distal end portion of the super-elastic wire to conform with the shape of that portion of the blood vessel at which said distal end portion is to be positioned.

The super-elastic wire used in the present invention is formed of an alloy which exhibits an apparent plastic deformation of several % to about 10%, if load is applied to the alloy under temperatures higher than the temperature at which the reverse transformation of the alloy is completed, and which is completely brought back to the original state upon removal of the load. It is most desirable to use a Ti-Ni alloy consisting essentially of 50.5 to 51.0 atomic % of Ni and the balance substantially Ti for forming the super-elastic wire. It is also possible to use a Ti-Ni alloy consisting essentially of 50.3 to 51.0 atomic % of Ni and the balance substantially Ti. Further, it is possible to use a so-called Ti-Ni-X series alloy, where "X" represents at least one kind of a third element.

In the catheter of the present invention, the super-elastic wire performs the function performed by a guide wire in the conventional catheter. Thus, the invented catheter can be easily inserted into a branched blood vessel such as a celiac artery without using a guide wire. It follows that the present invention permits simplification of the catheter introducing operation, and also permits alleviating the pain given to the patient. In addition, the time required for the catheter introduction can be shortened to less than about half the time required in the conventional catheter using a guide wire.

BEST MODE OF EMBODYING THE INVENTION

Figure 1:
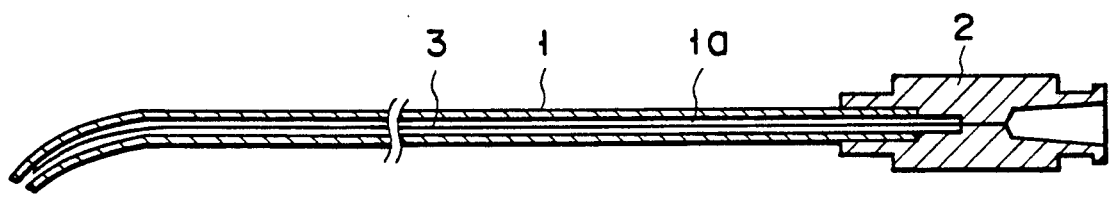
FIG. 1 is a cross sectional view showing a catheter for introduction into a blood vessel according to one embodiment of the present invention.
Figure 2:
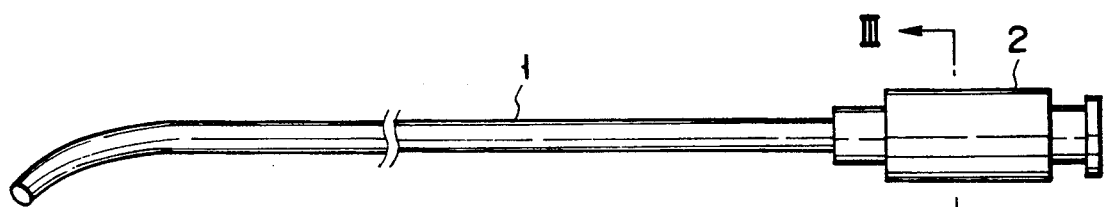
FIG. 2 is a side view of the catheter for introduction into a blood vessel shown in FIG. 1.

FIGS. 1 and 2 collectively show a catheter for introduction into a blood vessel according to one embodiment of the present invention. As seen from the drawings, the catheter comprises a tubular catheter body 1 having an inner diameter of 1.0 mm and a length of 800 mm, a lure tapered hub 2 fixed by fusion, an adhesive or the like to the proximal end of the catheter body 1, and a super-elastic wire 3 having an outer diameter of 0.6 mm and a length of 810 mm. The catheter body 1 is formed of a flexible synthetic resin such as nylon, polyurethane, fluorine resin, or soft fluorine resin. The hub 2 is also formed of a synthetic resin such as nylon. Further, the super-elastic wire 3, which extends through a lumen 1a of the catheter body 1 to reach the distal end region of the catheter body 1, is formed of a Ni-Ti alloy containing at least 50.3 atomic % of Ni.

Figure 3:
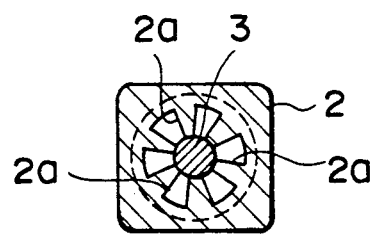
FIG. 3 is a cross sectional view along the line III—III shown in FIG. 2.

FIG. 3 illustrates as an example how to fix the super-elastic wire 3 within the hub 2. It is seen that the wire 3 is supported by the tip portions of a plurality of projections 2a radially projecting from the inner wall of the hub 2 toward the axis.

It is desirable to cover each of the superelastic wire 3 and the catheter body 1 with an urethane resin layer by the method as described in, for example, Unexamined Published Japanese Patent Application No. 31-45775, so as to modify the surface conditions of these wire 3 and catheter body 1. It is also desirable to cover the outer surfaces of the catheter body 1 and the super-elastic wire 3 with a layer of a water-soluble high molecular weight material such as polyvinyl pyrrolidone, sodium methylvinyl ether maleic anhydride, polyacrylamide hydrolyzate, sodium alginate, sodium polyvinyl sulfonate, ammonium salt of methylvinyl ether maleic anhydride or polyacrylamide quaternary compound. Further, it is also desirable to impart lubricity by wetting with water or an aqueous solution. For example, it is desirable to lightly wipe the surface of the catheter body 1 with gauze immersed in a heparinadded physiological saline so as to achieve lubrication with a water-soluble high molecular weight material.

Each of the catheter body 1 and the super-elastic wire 3 is somewhat bent at the distal end portion as shown in the drawings to conform with the shape of the blood vessel into which the catheter is to be introduced.

Further, an X-ray intransmissible material may be mixed into the catheter body 1 and the super-elastic wire 3 via the resin coating or the like. In this case, introduction into a blood vessel by utilizing, for example, an X-ray image forming apparatus.

For introducing the catheter of the present invention into a blood vessel, it is unnecessary to use a guide wire. Specifically, the catheter is introduced as it is into an artery having an introducing needle, an introducer, etc. retained therein. Under this condition, the hub is operated to transmit torque to the distal end of the catheter so as to achieve selection of passageway at a branched portion of the blood vessel such that the distal end of the catheter reaches a desired position within the blood vessel. Then, a medical solution, an image-forming agent, etc. is injected from the hub 2 into the blood vessel.

Figure 4:
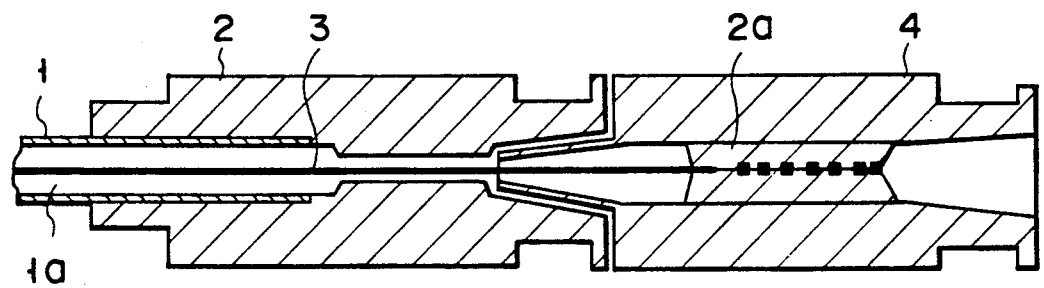
FIG. 4 is a cross sectional view showing in a magnified fashion the hub portion of a catheter according to another embodiment of the present invention.
Figure 5:
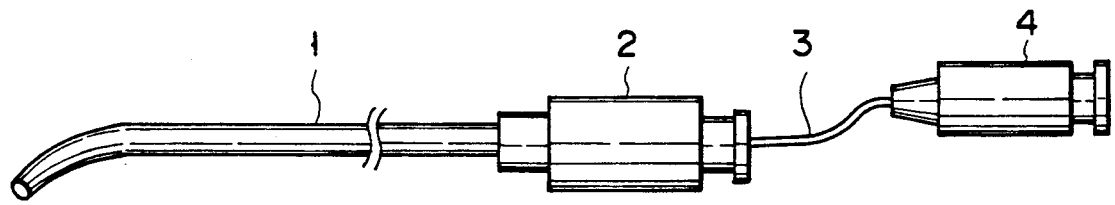
FIG. 5 is a side view showing how to use the catheter shown in FIG. 4.

FIGS. 4 and 5 collectively show a catheter according to another embodiment of the present invention. In this embodiment, the super-elastic wire 3 is detachable from the catheter body 1.

As seen from FIG. 4, the proximal end of the superelastic wire 3 is fixed to a hub 4 for fixing the wire 3, and the hub 4 is detachably coupled with the hub 2 of the catheter body 1. The super-elastic wire 3 can be fixed to the hub 4 by a method similar to that shown in FIG. 3. Thus, it is possible to withdraw the super-elastic wire 3 together with the hub 4 after introduction of the catheter body to the desired position within a blood vessel, as shown in FIG. 5. The withdrawal of the wire 3 results in an increased effective area of the lumen 1a of the catheter body, making it possible to increase the injection rate of a medical solution, an image-forming agent, etc. through the hub 2. The other construction is the same as that of the embodiment shown in FIGS. 1 to 3 and, thus, the description thereof is omitted.

Figure 6:
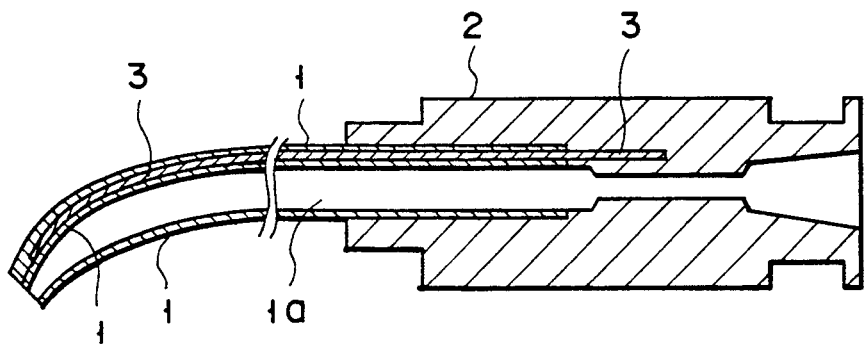
FIGS. 6 and 7 are cross sectional views each showing a catheter for introduction into a blood vessel according to still another embodiment of the present invention.

In each of the embodiments described above, the super-elastic wire extends through the lumen of the catheter body. However, the super-elastic wire may be embedded in the material forming the catheter body, as shown in, for example, FIG. 6. It is seen that the super-elastic wire 3 is embedded in the catheter body in a manner to extend in the longitudinal direction of the catheter body 1. Like the embodiment of FIG. 4, the embodiment of FIG. 6 also permits increasing the effective area of the lumen 1a. The other construction of FIG. 6 is the same as that of the embodiment shown in FIGS. 1 to 3. Thus, the same reference numeral are put in FIG. 6 to omit the description thereof.

Figure 7:
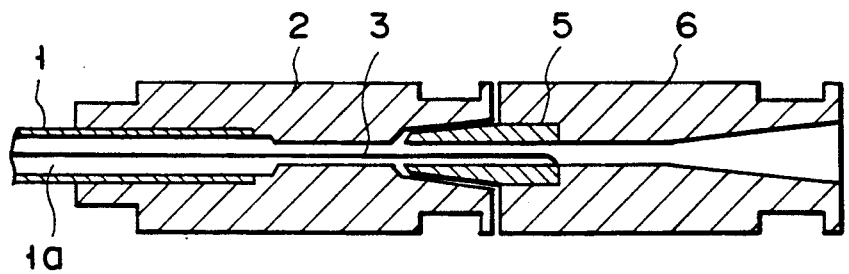

FIG. 7 shows a still another modification with respect to the technique of fixing the super-elastic wire. In this case, the connector for fixing the super-elastic wire comprises a lure tapered portion 5 and a connector body 6 having the lure tapered portion 5 mounted at the distal end portion. As seen from the drawing, the distal end portion of the super-elastic wire 3 is held at the junction between the lure tapered portion 5 and the connector body 6 so as to fix the super-elastic wire. The other construction of FIG. 7 is the same as that of the embodiment shown in FIGS. 1 to 3. Thus, the same reference numeral are put in FIG. 7 to omit the description thereof.

INDUSTRIAL APPLICABILITY

The catheter for introduction into a blood vessel according to the present invention is adapted for use in the treatment or inspection of a diseased portion within a blood vessel, particularly, adapted for injecting or withdrawing a liquid such as a medical solution and a contrast media or, in the case of applying an embolus operation, a thrombolic material such as a gelatine sponge into and out of the diseased portion.

We claim:

1. A catheter for introduction into a blood vessel, comprising:
    a catheter body having a lumen opening at a distal end of said catheter and provided at its proximal end with a first hub, said catheter body being covered on the outer surface thereof with a water-soluble high molecular weight material; and
    a super-elastic wire detachably inserted in said lumen of the catheter body and extended to reach a distal end region of the catheter body, said lumen having a diameter larger than said wire thereby defining a space around said wire for passage of a medical liquid through said lumen, and said wire being attached to a second hub which is detachably fitted in said first hub of the catheter body and has a passage therethrough in communication with said space for introducing a medical liquid through said first and second hubs, said space, and out of said opening, said super-elastic wire being covered with a synthetic resin layer having an X-ray non-transmission material mixed therein, and with a water-soluble high molecular weight material covering said synthetic resin layer.

2. The catheter for introduction into a blood vessel according to claim 1, wherein an X-ray non-transmission material is mixed in the resin coating of the super-elastic wire.

3. The catheter for introduction into a blood vessel according to claim 1, wherein the distal end portion of the super-elastic wire is bent to conform with the shape of that portion of blood vessel at which said distal end portion is to arrive.

4. The catheter for introduction into a blood vessel according to claim 1, wherein an X-ray non-transmission material is mixed in the catheter body.

5. A catheter for introduction into a blood vessel, comprising:
   a catheter body having a lumen opening at a distal end of said catheter and provided at its proximal end with a hub, said catheter body being covered on the outer surface thereof with a water-soluble high molecular weight material; and
   a super-elastic wire detachably inserted in said lumen of the catheter body, leaving a space around said wire for passage of a medical liquid through said lumen, and said wire being attached to a hub which is detachably fitted in said hub of the catheter body and has a passage for introducing a medical liquid therethrough, said super-elastic wire being covered with a synthetic resin layer having an X-ray non-transmission material mixed therein, and with a water-soluble high molecular weight material covering said synthetic resin layer.

* * * * *